United States Patent [19]

Rife

[11] 3,954,977

[45] May 4, 1976

[54] INSECTICIDAL PYRETHROID COMPOSITIONS HAVING INCREASED EFFICACY

[75] Inventor: Harold E. Rife, Millington, N.J.

[73] Assignee: American Home Products Corporation, New York, N.Y.

[22] Filed: Feb. 19, 1974

[21] Appl. No.: 443,583

Related U.S. Application Data

[63] Continuation-in-part of Ser. No. 274,556, July 24, 1972, abandoned.

[52] U.S. Cl. .............................. 424/188; 424/186; 424/189; 424/191; 424/306; 424/312; 424/320; 424/365
[51] Int. Cl.² .......................................... A01N 9/08
[58] Field of Search ........... 424/186, 188, 189, 191, 424/306, 320

[56] References Cited
UNITED STATES PATENTS

| | | |
|---|---|---|
| 2,166,120 | 7/1939 | Bousquet ..................... 424/191 X |
| 2,300,612 | 11/1942 | Christmann et al. ............... 424/189 |
| 2,386,779 | 10/1945 | Coleman et al. .................... 424/191 |
| 2,432,607 | 12/1947 | Brown .............................. 424/189 |
| 2,564,606 | 8/1951 | Percey et al. .................... 424/189 X |
| 2,792,328 | 5/1957 | Solec ................................. 424/188 |
| 2,841,521 | 7/1958 | Abramitis ...................... 424/191 X |
| 3,186,903 | 6/1965 | Soltes ............................... 424/189 |
| 3,342,673 | 9/1967 | Kaufman et al. ............... 424/300 X |

Primary Examiner—Leonard Schenkman
Attorney, Agent, or Firm—Stephen Venetianer

[57] ABSTRACT

Insecticidal compositions are described containing natural and/or synthetic pyrethroids, an emulsifier and a N,N-(lower)alkyl fatty acid amide. The use of the emulsifier system described herein prolongs the residual insecticidal pyrethroid activity.

2 Claims, No Drawings

INSECTICIDAL PYRETHROID COMPOSITIONS HAVING INCREASED EFFICACY

This application is a continuation-in-part of Ser. No. 274,556, filed on July 24, 1972 now abandoned.

The present invention relates to pyrethroid containing compositions having prolonged residual insecticidal activity.

The pyrethrins are a mixture of pyrethroids which are extracted from the pyrethrum plant, Chrysanthemum cinerariaefolium. The pyrethrum extract, which consists of pyrethrins I and II and Cinerin I and II (see U.S. Pat. No. 3,186,903 for structural formulas) is a very effective insecticide against a wide variety of insects. It is a relatively non-toxic insecticide with the excellent properties of quick knockdown and kill of insects. Synthetic Pyrethroids have also been synthesized which have similar properties to natural pyrethrins. Examples of some of these are allethrin, d-trans allethrin, tetramethrin, furethrin, resmethrin and d-trans resmethrin.

While the immediate effectiveness of pyrethrins and synthetic pyrethroids is excellent, their power to maintain knockdown control (i.e. bring about paralysis of the insects to be controlled for a long period of time) is not impressive. This is reported in the art as due to their instability (rapid breakdown and volatility) under the effect of light, moisture, air heat and alkali meterials, soap, etc. Consequently, these insecticides have a short residual life and period of effectiveness.

A substantial amount of work has been done to render pyrethrins more widely useful by combining them with certain chemicals which are synergists for pyrethroids. A description of such chemicals may be found in the literature as exemplified by U.S. Pat. Nos. 3,035,969; 2,955,071 and 2,792,328. However, even where natural pyrethrins and/or synthetic pyrethroids are combined with synergistic agents, the residual activity of such compositions is not substantially affected.

The present invention provides novel insecticidal compositions containing a natural pyrethrin and/or synthetic pyrethroid having substantial prolonged residual insecticidal activity without loss of the quick knockdown and kill characteristics associated with pyrethroid insecticides. Accordingly, the compositions of this invention because of their residual activity are particularly effective against crawling insects.

As used throughout this application, the term "pyrethroid" embraces natural pyrethrins as well as synthetic pyrethrum like materials.

The insecticidal composition of the present invention consists essentially of (a) an insecticidal effective amount of a pyrethroid, preferably about 0.1 to about 1.5% by weight of a pyrethroid, (b) zero to about 15% by weight of a pyrethroid synergist, (c) about 0.2 to about 6% by weight of at least one emulsifier, preferably not more than about 2.5% by weight, (d) about 0.5 to about 8% by weight of a N,N-di(lower)alkyl fatty acid amide and (e) about 70 to about 98% by weight of a carrier, either liquid and/or solid. Where a pyrethroid synergist is present, the use of a pyrethroid synergist is dependent on the type of pyrethroid selected. For example, if a resmethrin or d-trans resmethrin is used, no pyrethroid synergist is required. With natural pyrethroids and other synthetic pyrethroids, preferably 0.5 to about 10% by weight of a pyrethroid synergist is used. The weight ratio of pyrethroid to pyrethroid synergist in the composition is preferably between about 1:2.5 to about 1:10, more preferably about 1:5 to 1:8. The weight ratio of the N,N-di(lower)alkyl fatty acid amide to the pyrethroid is about 10:1 to about 1:2, preferably about 7:1 to 2:1.

Suitable pyrethroids useful in the present invention are illustrated by pyrethrum extract which consists of pyrethrins I and II and cinerin I and II; synthetic pyrethroids such as allethrin, d-trans allethrin, tetramethrin, furethrin, resmethrin, etc.

The selection of a pyrethroid synergist is well within the skill of the art since such materials and their properties are described in the insecticide art. Illustrative of such materials are piperonyl butoxide, piperonyl cyclonene, n-octyl sulfoxide of isosafrole, n-propyl isome, N-isobutyl-10 undecylenamide, sesamin, 4-indanyl-N-heptyl carbonate, etc.

The emulsifier system is composed of one or more surface active agents that form water-in-oil emulsions. The non-ionic water-soluble materials are preferred. These emulsifiers are illustrated by sorbitol, sorbitan and/or sorbide esters of fatty acids containing at least ten carbon atoms, condensation products of ethylene oxide with fatty acid esters, alkylaryl polyoxyethylene glycol ethers. Illustrative of specific emulsifiers are sorbitan sesquioleate, sorbide dioleate, sorbitan trioleate, sorbitan trioleate polyoxyalkylene, nonylphenoxypoly(ethyleneoxy)ethanol, etc. The preferred emulsifier is a combination of sorbide dioleate and polyglycerol ester of oleic acid.

The N,N-di(lower)alkyl fatty acid amides within the scope of the present invention have from $C_6$ to $C_{20}$ carbon atoms and are illustrated by N,N-dimethyl oleamide, N,N-dimethyl arachid amide, N,N-dimethylstearamide, N,N-dimethylmyristamide, N,N-dimethylpalmitamide, N,N-dimethyllinoleamide, N,N-dimethylcaprylamide, etc. The preferred amide is N,N-dimethyloleamide.

The insecticidal compositions of the present invention include a carrier which may be a liquid or solid, a liquid carrier being preferred. The term "carrier" as used herein means a material which may be organic or inorganic and synthetic or of natural origin with which the active substances are mixed to facilitate its storage, handling and/or its application to the object to be treated. The preferred liquid carrier is water; however, up to about 20% by weight of a non-aqueous carrier may be used in formulating the insecticide composition in combination with water. The non-aqueous carrier may be any of the usual pyrethroid solvents such as naphtha, petroleum distillates, benzene, light lubricating oil fractions, etc. Examples of suitable solid carriers for the insecticidal components include talc, gypsum, diatomite, wood, flour, etc.

The compositions of the present invention may include as optional ingredients materials such as corrosion inhibitors (e.g. epoxylated oil); biologically active substances such as other insecticides (e.g. retenone, endrin, dieldrin, aldrin, etc.); stabilizers such as sodium benzoate, etc.

The insecticidal compositions of the present invention are preferably packaged in a self-contained, valve-controlled aerosol unit which provides a fine spray upon activation of the valve. The aerosol container unit consists of a pressure-tight aerosol container having a valve-controlled opening and containing a composition as set forth herein and from about 20% to about 50% of a propellant. Propellants such as isobutane, isobutane/propane, dichlorodifluromethane, trichlorofluoromethane, dichlorotetrafluoroethane or mixtures thereof. The propellant should be effective at atmospheric temperature and not adversely react with any components of the composition.

The following examples are illustrative of the insecticidal compositions of the present invention.

Example 1

| Ingredient | % by Weight |
|---|---|
| pyrethrum extract (20%) | 1.55 |
| piperonyl butoxide | 1.55 |
| isoparaffinic petroleum base oil ("Shell-Sol 71") | 3.00 |
| polyglycerol ester of oleic acid | 0.60 |
| sorbide dioleate | 0.40 |
| N,N-dimethyl oleamide | 1.50 |
| epoxylated oil ("Epoxol-95") | 0.50 |
| deionized water | 55.90 |
| propane | 5.25 |
| isobutane | 29.75 |

The isoparaffinic petroleum base oil is added to a mixing tank followed by the consecutive addition of the pyrethrum extract, piperonyl butoxide, polyglycerol ester of oleic acid, sorbide dioleate, N,N, dimethyl oleamide and epoxylated oil, respectively. The contents of the tank are agitated until the mixture is homogenous.

The foregoing mixture is added to an aerosol container followed by the addition of the deionized water. Thereafter, the propellant mixture is charged to the container using either the "thru the valve" or "under the cap" methods.

The composition of Example 1 was coated onto a series of 6×6 foot panels and biological tests were conducted with the tested panels stored at ambient room temperature in daylight but in the absence of sunlight using the last instar nymph of the German cockroach as the test insect. On each panel coated with the test composition 20 German cockroaches were caged at different times after treatment of the panel to determine the percent knockdown. These tests indicate the residual activity of the composition as well as the knockdown rate. The results are reported in Table 1 below.

Table 1

| Surface | Dosage of Pyrethrins on Surface (Mgs./sq.ft.) | Age of Treated Panel (Days)* | % Knock down & Mortality Hours | | |
|---|---|---|---|---|---|
| | | | 1 | 24 | 48 |
| Glass | 12.5 | 14 | 100 | — | — |
| | | 28 | 100 | — | — |
| Plywood | 12.5 | 7 | 0 | 60 | 100 |
| | 12.5 | 14 | 0 | 50 | 100 |
| | 12.5 | 21 | 20 | 30 | 30 |
| | 12.5 | 28 | 0 | 10 | 10 |
| | 25 | 7 | 0 | 60 | 100 |
| | 25 | 14 | 0 | 50 | 100 |
| | 25 | 21 | 60 | 70 | 80 |
| | 25 | 28 | 0 | 20 | 20 |
| Vinyl Tile | 25 | 7 | 10 | 70 | 100 |
| | 25 | 14 | 0 | 80 | 100 |
| | 25 | 21 | 0 | 10 | 30 |
| | 25 | 28 | 0 | 40 | 50 |
| Linoleum | 25 | 7 | 10 | 90 | 100 |
| | 25 | 14 | 0 | 30 | 30 |
| | 25 | 21 | 30 | 80 | 80 |

Table 1-continued

| Surface | Dosage of Pyrethrins on Surface (Mgs./sq.ft.) | Age of Treated Panel (Days)* | % Knock down & Mortality Hours | | |
|---|---|---|---|---|---|
| | | | 1 | 24 | 48 |
| | 25 | 28 | 0 | 0 | 0 |

*The number of days the panels treated with the insecticidal composition were exposed to daylight prior to placing cockroaches on panel.

6×6 foot plywood panels were also coated with a composition as described in Example 1, except that the N,N-dimethyl oleamide was omitted at a dosage of 12.5 mg/sq. ft. and compared with the composition of Example 1 at the same dosage. The results are reported in Table 2 on the following page.

| Product | Age of Panels Treated (Days) | % Knock down and Mortality (hours) | | |
|---|---|---|---|---|
| | | 1 | 24 | 48 |
| Composition of Example 1 | 1 | 20 | 100 | — |
| Composition of Example 1 | 7 | 0 | 60 | 100 |
| Composition of Example 1 | 14 | 0 | 50 | 100 |
| Composition without N,N-dimethyl oleamide | 1 | 0 | 30 | 100 |
| Composition without N,N-dimethyl oleamide | 7 | 0 | 10 | 40 |
| Composition without N,N-dimethyl oleamide | 14 | 0 | 0 | 0 |

The compositions of the present invention are particularly adapted for killing flying insects such as mosquitos and gnats; crawling insects such as roaches, ants, spiders, waterbugs and centipedes; and garden insects such as aphids, red spider mites and Japanese beetles.

What is claimed is:

1. An insecticidal composition comprising (a) about 0.1 to about 1.5% to weight of a pyrethroid, (b) about 0.5 to about 15% by weight of piperonyl butoxide, (c) about 0.2 to about 2.5% by weight of a non-ionic water soluble emulsifier, wherein said emulsifier is a mixture of sorbide dioleate and a polyglycerol ester of oleic acid, (d) about 0.5 to about 8% by weight of N,N-dimethyloleamide, and about 70 to about 98% by weight of a aqueous carrier for said pyrethroid the weight ratio of said pyrethroid to said piperonyl butoxide being about 1:2.5 to about 1:10 and the weight ratio of said N,N-dimethyloleamide to said pyrethroid being about 10:1 to about 1:2.

2. A method of killing crawling insects comprising applying to a surface an effective amount of the following insecticidal composition having residual insecticidal activity:
   (a) about 0.1 to about 1.5% to weight of a pyrethroid, (b) about 0.5 to about 15% by weight of piperonyl butoxide, (c) about 0.2 to about 2.5% by weight of a non-ionic water soluble emulsifier wherein said emulsifier is a mixture of sorbide dioleate and a polyglycerol ester of oleic acid, (d) about 0.5 to about 8% by weight of N,N-dimethyloleamide and (e) about 70 to about 98% by weight of a aqueous carrier for said pyrethroid, the weight ratio of said pyrethroid to said piperonyl butoxide being about 1:2.5 to about 1:10 and the weight ratio of said N,N-dimethyloleamide to said pyrethroid being about 10:1 to about 1:2.

* * * * *